United States Patent
Kozel et al.

(10) Patent No.: US 10,925,302 B2
(45) Date of Patent: *Feb. 23, 2021

(54) PEROXIDE DISPERSIONS

(71) Applicant: Arkema Inc., King of Prussia, PA (US)

(72) Inventors: Thomas H Kozel, Pottstown, PA (US); Joseph M. Gravelle, Spring City, PA (US); Timothy Belford, Coatesville, PA (US); Tomas Salvador, Sugar Land, TX (US); Marina Despotopoulou, Havertown, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/825,377

(22) Filed: Nov. 29, 2017

(65) Prior Publication Data

US 2018/0077954 A1 Mar. 22, 2018

Related U.S. Application Data

(63) Continuation of application No. 14/013,196, filed on Aug. 29, 2013, now Pat. No. 9,861,119, which is a continuation-in-part of application No. PCT/US2013/028492, filed on Mar. 1, 2013.

(60) Provisional application No. 61/660,148, filed on Jun. 15, 2012.

(51) Int. Cl.

| | |
|---|---|
| A61K 9/14 | (2006.01) |
| A61K 8/38 | (2006.01) |
| A61K 8/39 | (2006.01) |
| C11D 1/74 | (2006.01) |
| A61Q 5/08 | (2006.01) |
| A61Q 11/00 | (2006.01) |
| A61K 8/02 | (2006.01) |
| A61K 8/04 | (2006.01) |
| C11D 3/39 | (2006.01) |
| C11D 17/00 | (2006.01) |
| A61K 47/08 | (2006.01) |
| A23L 5/49 | (2016.01) |
| C11D 3/395 | (2006.01) |
| A23L 5/40 | (2016.01) |

(52) U.S. Cl.
CPC ........ *A23L 5/40* (2016.08); *A23L 5/49* (2016.08); *A61K 8/0241* (2013.01); *A61K 8/044* (2013.01); *A61K 8/38* (2013.01); *A61K 8/39* (2013.01); *A61K 9/14* (2013.01); *A61K 9/145* (2013.01); *A61K 47/08* (2013.01); *A61Q 5/08* (2013.01); *A61Q 11/00* (2013.01); *C11D 1/74* (2013.01); *C11D 3/3947* (2013.01); *C11D 3/3951* (2013.01); *C11D 3/3955* (2013.01); *C11D 3/3956* (2013.01); *C11D 17/0013* (2013.01); *A61K 2800/412* (2013.01); *A61K 2800/652* (2013.01)

(58) Field of Classification Search
CPC ... C11D 3/3955; C11D 3/3956; C11D 3/3947; C11D 17/0013; A61Q 5/08; A61Q 11/00; A61K 8/044; A61K 8/38; A61K 9/14; A61K 47/08; A61K 2800/412; A61P 31/04; A61P 31/00; A61P 17/10
See application file for complete search history.

(56) References Cited

U.S. PATENT DOCUMENTS

| | | |
|---|---|---|
| 2,684,971 A | 7/1954 | Alsop et al. |
| 3,397,245 A | 8/1968 | Appell |
| 3,507,800 A | 1/1970 | Leveskis |
| 3,825,509 A | 7/1974 | Miller |
| 3,843,801 A | 10/1974 | Efthymiou |
| 4,039,475 A | 8/1977 | Oosterwijk et al. |
| 4,092,470 A | 5/1978 | Oosterwijk et al. |
| 4,440,885 A | 4/1984 | Tamosauskas |
| 4,734,135 A | 3/1988 | Satomi et al. |
| 4,842,765 A | 6/1989 | Satomi |
| 4,888,184 A | 12/1989 | Bottomley et al. ............. 426/41 |
| 5,110,495 A | 5/1992 | Self |
| 5,300,600 A | 4/1994 | Bock et al. |
| 5,478,490 A | 12/1995 | Russo et al. |
| 5,690,856 A | 11/1997 | Milleville et al. |
| 5,871,800 A | 2/1999 | George et al. |

(Continued)

FOREIGN PATENT DOCUMENTS

| | | |
|---|---|---|
| FR | 378.515 | 6/1907 |
| GB | 328544 | 4/1930 |

(Continued)

OTHER PUBLICATIONS

Drugs.com, "Potassium Citrate," Drug Information Online, <http://www.drugs.com/potassium_chloride.html>, published Jul. 14, 2010, p. 1-4.*

(Continued)

*Primary Examiner* — Monica A Shin

(74) *Attorney, Agent, or Firm* — Lynn B. Morreale

(57) ABSTRACT

The viscosity of aqueous dispersions of normally solid organic peroxides may be advantageously lowered through the use of surfactants which are polyglyceryl esters of C6-C12 fatty acids. The reduction in viscosity facilitates milling the peroxides to reduce particle size and also provides dispersions of small particle size peroxides which may be readily poured or pumped. The aqueous dispersions are useful as components of pharmaceutical, personal care, and cleaning products and the like and are effective decolorizing agents for food products, industrial products and the like.

17 Claims, No Drawings

(56) References Cited

U.S. PATENT DOCUMENTS

| | | | |
|---|---|---|---|
| 6,113,921 A * | 9/2000 | Friedman | A61M 35/00 |
| | | | 424/400 |
| 6,120,820 A | 9/2000 | Brody et al. | |
| 8,697,130 B1 | 4/2014 | Gerlach et al. | |
| 2003/0104021 A1* | 6/2003 | Burnier | A61K 8/26 |
| | | | 424/401 |
| 2004/0101566 A1 | 5/2004 | Cooper et al. | |
| 2004/0185066 A1* | 9/2004 | Uang | C09K 5/20 |
| | | | 424/400 |
| 2005/0118320 A1 | 6/2005 | Doyle | 426/573 |
| 2010/0261795 A1 | 10/2010 | Buzot | |
| 2011/0003894 A1 | 1/2011 | Louis | A61K 8/38 |
| | | | 514/569 |
| 2011/0086959 A1 | 4/2011 | Kozel et al. | |
| 2012/0010352 A1 | 1/2012 | O | |
| 2012/0157366 A1 | 6/2012 | Anim-Danso et al. | |
| 2012/0196843 A1 | 8/2012 | Fares et al. | |
| 2013/0143786 A1 | 6/2013 | Zhu et al. | |

FOREIGN PATENT DOCUMENTS

| | | |
|---|---|---|
| GB | 1156573 | 7/1969 |
| WO | WO 03/066021 A2 | 8/2003 |
| WO | WO 2012/170866 A1 | 12/2012 |
| WO | WO 2013/187949 A1 | 12/2013 |

OTHER PUBLICATIONS

RxMed, "Calcium Chloride Injection USP," <http://www.rxmed.com/b.main/b2.pharmaceutical/b2.1.monographs/CPS-%20Monographs/CPS-%20(General%20Monographs-%20C)/CALCIUM%20CHLORIDE%20INJECTION%20USP.html>, published Jul. 4, 2008, p. 1-4.*

Some Factors Affecting the Action of Benzoyl Peroxide in the Bleaching of Milk and Cream for Blue Cheese Manufacture; S. Kuramoto & J. J. Jezeski—Department of Dairy Husbanry, University of Minnesota, St. Paul.; pp. 1241-1246—Jun. 4, 1954.

American Dairy Science Association—Effect of Temperature and Bleaching Agent on Bleaching of Liquid Cheddar Whey; M.A.D. Listiyani, R.E. Campbell, R. E. Miracle, D. M. Barano, P. D. Gerard & M. A. Drake. J. Dairy Sci. 95 pp. 36-49.

Oil and Fat Industries—Jun. 1928—Orgainc Peroxides as Bleaching Agents—Thier Application in the Oil and Fat Industries . . . , F. Visser't Hooft pp. 180182.

Crosfield—Sorbsil Silicas; Edible Oil Operator Training—John Lenke, Crosfield Company—Products Chimiques CCC Itee Canada Color and Chemicals (Eastern) Limited—pp. 1-12.

Research Vote No. 74198—Centre of Lipids Engineering and Applied Research (Clear) Univorid Teknologi Malaysia—Nov. 2006—Prof. Madya Dr. Noor Azian Morad, Prof. Mayda Mustafa Kamal Abd Aziz, Rohani binti Mohd Zin—Process Design in Degumming and Bleaching of Palm Oil—pp. 1-239.

Benzoyl Peroxide—Chemical and Technical Assessment (CTA), 61st JECFA , FOA 2004 pp. 1(6)-6 (6)—Bleaching Agent in Flour, Whey Processing and Milk for Italian Cheese Making—Yehia El-Samragy.

American Dairy Science Association—Effect of Temperature and Bleaching Agent on Bleaching of Liquid Cheddar Whey; M.A.D. Listiyani, R.E. Campbell, R. E. Miracle, D. M. Barano, P. D. Gerard & M. A. Drake. J. Dairy Sci. 95 pp. 36-49, published 2012.

Cyber Lipid, "Polyglyceryl Esters," <http://www.cyberlipid.org/glycer/glyc0013.htm>, published Apr. 8, 2010, p. 1-2.

A. Imeson, "Food Stabilisers, Thickeners and Gelling Agents," © 2010 by Blackwell Publishing Ltd., p. 1-3.

D. Saha et al., "Hydrocolloids as thickening and gelling agents in food: a critical review," J Food Sci Technol (Nov.-Dec. 2010) 47(6):587-597.

Lonza, "Polyaldo 10-1-CC-KFG (Non GMO)," http://bio.lonza.com/uploads/tx_mwaxmarketingmaterial/Lonza_ProductDataSheets_Polyaldo_10-1-CC_KFG_NON_GMO_PDS.pdf>, Revised May 3, 2010, p. 1-2.

* cited by examiner

PEROXIDE DISPERSIONS

CROSS-REFERENCE TO RELATED APPLICATIONS

This application is a continuation of and claims priority to U.S. Ser. No. 14/013,196, filed Aug. 29, 2013 which is a continuation-in-part of and claims priority to International Application No. PCT/US2013128492, filed Mar. 1, 2013, which claims priority from U.S. Provisional Application No. 61/660,148, tiled Jun. 15, 2012, each of which is incorporated herein by reference in its entirety for all purposes.

FIELD OF INVENTION

The present invention relates to aqueous dispersions of normally solid organic peroxides. The dispersions are pastes or liquids which contain high concentrations of the peroxide, wherein the peroxide is present in the form of small particles (e.g., less than 10 µm diameter on average). The pastes are shear thinning or sufficiently flowable so as to be pumpable, pourable, and/or sprayable, which makes their handling and use easier. The invention further provides methods of using such aqueous dispersions, as well as compositions containing the aqueous dispersions.

BACKGROUND

Peroxides have, as a general property, a tendency to be flammable and explosive with some peroxides exhibiting such properties to a greater extent than others. For example, benzoyl peroxide may decompose when dry due to shock, friction, or static electricity. This property carries with it the hazards to the users of these materials as well as to the manufacturers and intermediate handlers thereof. Accordingly, it has long been an object to provide flame resistant organic peroxide compositions.

The safety and end-use advantage provided by water-soluble or water-dispersible peroxides has been recognized. However, many peroxides of commercial interest are water insoluble. Moreover, dispersions containing relatively high concentrations of water insoluble, solid peroxides are typically quite viscous and therefore difficult to handle and process. This problem is particularly aggravated as the particle size of the peroxide is reduced. For example, when milling a peroxide in water to reduce its particle size below 10 µm, the aqueous dispersion often forms a very thick paste. Further milling becomes quite difficult unless milling is discontinued for a period of time to permit the dispersion to "relax" and soften to an extent where milling again becomes feasible. These difficulties significantly lengthen the period of time necessary to achieve a desired small particle size. As there are many end use applications for water insoluble peroxides where smaller particle size will be advantageous, there remains a need for highly concentrated aqueous dispersions of small particle size peroxides which are capable of being handled by pumping and/or pouring as well as methods by which such aqueous dispersions may be conveniently and efficiently prepared.

Water-insoluble, solid organic peroxides such as benzoyl peroxide are widely used as bleaching agents, for example in the decolorization of food products such as flour, whey and cheese. See Yehia EI-Samragy, "Benzoyl Peroxide— Chemical and Technical Assessment (CTA)," 61$^{st}$ JECFA, 2004.

BRIEF SUMMARY OF THE INVENTION

The present invention provides an aqueous dispersion comprising a) about 40% by weight or more of a water-insoluble, solid organic peroxide having an average particle size of less than 10 µm and b) a surfactant which is a polyglyceryl ester of one or more C6-C18 fatty acids. In another aspect, the invention provides a process for making such an aqueous dispersion, comprising milling an organic peroxide having an average particle size of greater than 10 µm in water in the presence of a surfactant which is a polyglyceryl ester of one or more C6-C18 fatty acids. Using such a surfactant helps to reduce the viscosity of the aqueous dispersion during processing.

The aqueous dispersions of the present invention have an advantage of being in liquid, readily pumpable, sprayable and/or pourable form, thereby avoiding the problems traditionally associated with handling or using organic peroxides in dry, particulate form or in dispersions of high viscosity.

According to another aspect of the invention, a product such as a food product or a non-food industrial product may be decolorized by a method comprising contacting the product with the aforementioned aqueous dispersion.

A pharmaceutical composition is provided in another aspect of the invention that is comprised of the aforementioned aqueous dispersion and at least one additional pharmaceutically acceptable ingredient.

Still another aspect of the invention relates to a personal care composition comprised of the aforementioned aqueous dispersion and at least one additional personal care ingredient.

The preset invention additionally furnishes a cleaning product that is comprised of the aforementioned aqueous dispersion and at least one additional cleaning product ingredient.

DESCRIPTION OF VARIOUS EMBODIMENTS OF THE INVENTION

Aqueous dispersions of the present invention comprise an organic peroxide which is normally solid (i.e., a solid at room temperature) and a surfactant.

Exemplary of suitable organic peroxides are aromatic diacyl peroxides, such as benzoyl peroxide, o-methylbenzoyl peroxide, o-methoxybenzoy I peroxide, o-ethoxy benzoyl peroxide, o-chlorobenzoyl peroxide and 2,4-dichlorobenzoyl peroxide; aliphatic diacyl peroxides, such as decanoyl peroxide, lauroyl peroxide and myristoyl peroxide; ketone peroxides, such as 1-hydroxy cyclohexyl peroxide and 1-hydroperoxycyclohexyl peroxide; aldehyde peroxides such as 1-hydroxy heptyl peroxide; peroxy dicarbonates such as dicetyl peroxydicarbonate, di(4-t-butylcyclohexyl) peroxydicarbonate and acylperoxy alkylcarbonates, such as acetyl peroxy stearyl carbonate and the like and mixtures thereof. Other organic peroxides which are normally solid at room temperature and substantially insoluble in water may also be employed. The starting organic peroxide may be obtained by any suitable method and may be in solid (dry) form or in the form of a mixture with water. As will be described in more detail hereafter, the organic peroxide typically has a relatively large particle size to begin with (e.g., greater than 10 µm) and then is reduced in size through any suitable procedure in the presence of the surfactant and water to provide the aqueous dispersions of the invention.

The present aqueous dispersions comprise about 35 percent or more by weight of an organic peroxide. One of the features of the present invention is that it enables the preparation of aqueous dispersions containing about 35 or more percent by weight of organic peroxide, wherein the dispersions are pumpable, sprayable, or pourable because they are shear thinning or flowable liquids. Heretofore it has been difficult to make pumpable or sprayable dispersions containing about 35 or more percent by weight organic peroxide. In this description, shear thinning means that viscosity drops as the shear rate increases. Thus, the viscosity of the peroxide dispersions of the present invention will drop as the dispersion is stirred or mixed and it becomes pourable or pumpable or sprayable, easing use. In some embodiments of the invention, the aqueous dispersion is sufficiently fluid such that it is capable of being poured, pumped, or sprayed, even without being subjected to stirring or mixing. The concentration of the peroxide in the aqueous dispersion may be adjusted as may be desired or needed, but typically the organic peroxide concentration is at least about 30 weight percent but not greater than about 75 weight percent, or between about 35 to 60 weight percent, or between about 37 to not greater than about 53 weight percent, or between about 37 to about 42 weight percent.

Sufficient water is present to provide an aqueous dispersion, with water acting as a liquid matrix within which particles of the organic peroxide are dispersed. Typically, the water content of the aqueous dispersion is from about 25 to 70 weight percent, from about 40 to 65 weight percent, from about 42 to about 63 weight percent, or from about 53 to about 63 weight percent, or from about 58 weight percent to about 63 weight percent. The pH of the water may be adjusted as may be desired or needed by the addition of one or more pH adjusting agents such as bases, acids, buffers and the like. Soluble species such as salts may also be present.

Besides the water and organic peroxide, the composition of the present invention also comprises one or more surfactants. In one embodiment, the surfactant is a pharmaceutically acceptable surfactant. A pharmaceutically acceptable surfactant refers to a surfactant that does not cause significant irritation to an organism and does not abrogate the biological activity and properties of an administered compound that the dispersion of the present invention is combined with. In another embodiment, the surfactant is a food grade surfactant. A food grade surfactant refers to a surfactant which is permitted by regulation to be present in a foodstuff, at least up to certain levels. The surfactant used may be both a pharmaceutically acceptable surfactant and a food grade surfactant.

It has now been surprisingly discovered that polyglyceryl esters of one or more C6-C18 fatty acids, or preferably polyglyceryl esters of one or more C6-C12 fatty acids, or preferably polyglyceryl esters of one or more C8-C12 fatty acids, are particularly effective in providing dispersions which remain free flowing liquids during the milling process used to reduce the average particle size of the organic peroxide to below 10 µm and preferably above 2 µm. That is, the use of other types of surfactants leads to the formation of very thick pastes during milling that significantly increases the time needed, to achieve a particular desired small particle size. The present invention thus provides substantial improvement in processing efficiency.

Polyglyceryl esters of fatty acids are also referred to in the art as "polyglycerol esters of fatty acids" and "polyglycerol fatty acid esters." They may be described as mixed partial esters formed by reacting polymerized glycerols with edible fats, oil or fatty acids. Commercial surfactants which are polyglyceryl esters of fatty acids may include minor amounts of mono-, di- and tri-glycerides, free glycerol and polyglycerols, free fatty acids and/or salts of free fatty acids. The degree of polymerization of the polyglyceryl component may vary. In various embodiments of the present invention, the polyglyceryl segment of the surfactant may contain at least 2, 3, 4, 5, 6, 7, 8 or 9 and/or not more than 20, 19, 18, 17, 16, 15, 14, 13, 12 or 11 glyceryl repeating units on average per molecule. In one particular embodiment, about 10 glyceryl repeating units per molecule on average are present.

It has been unexpectedly discovered that using polyglyceryls esterified with relatively short chain fatty acids as surfactants in a process wherein a relatively large particle size organic peroxide (e.g., having an average particle size greater than 10 µm) is milled in water to a smaller particle size (e.g., less than 10 µm or less than 5 µm average particle size and in some embodiments preferably greater than 2 µm average particle size) helps to lower viscosity during such a milling process. The resulting aqueous dispersion is shear thinning. The fatty acids used to esterify the polyglyceryl thus are predominantly C6-C18 fatty acids, or C6-C12 fatty acids, or C8-C12 fatty acids (i.e., fatty acids containing 6 to 18, or 6 to 12, or 8 to 12 carbon atoms per molecule), although minor amounts of shorter and/or longer chain fatty acids may also be present in the esterified polyglyceryl. For example, in various embodiments of the invention, at least 50, at least 60, at least 70, at least 80, at least 90 or essentially all of the fatty acid moieties present in the surfactant are C6-C18 or C6-C12 fatty acid moieties. Mixtures of different C6-C18, or C6-12, C8-C12, fatty acid moieties may be present. The fatty acid moieties may be straight chain or branched, saturated or unsaturated. Typically, the fatty acid moieties are monocarboxylate moieties corresponding to the general structure —OC(═O)R, where R is a C5-C11 alkyl group. In one embodiment, the fatty acid moieties present in the surfactant are predominantly saturated, such that the iodine value of the surfactant is less than 10 or less than 5. Examples of suitable C6-C18 fatty acids include, but are not limited to, hexanoic acid (also known as caproic acid), octanoic acid (also known as caprylic acid), decanoic acid (also known as capric acid) and dodecanoic acid (also known as lauric acid), tetradecanoic acid (also known as myristic acid) hexadecanoic acid (also known palmitic), octadecanoic (also known as steraric acid) and mixtures thereof. In one embodiment, the C6-C12 fatty acid is a mixture of octanoic acid and decanoic acid. (with other fatty acids possibly being present in minor amounts).

Typically, the polyglyceryl is partially esterified with fatty acid moieties, with one or more hydroxyl groups remaining unesterified. For example, the surfactant may contain an average of 1 to 3 fatty acid moieties per molecule. In certain embodiments, from about 25% to about 60%, or from about 30% to about 50%, of the available hydroxyl groups in the polyglyceryl are esterified with fatty acid moieties.

The surfactant may correspond to the general structure (I):

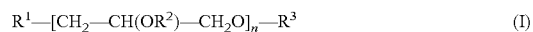

$$R^1—[CH_2—CH(OR^2)—CH_2O]_n—R^3 \quad (I)$$

wherein the average value of n is from about 6 to about 14 and $R^1$, $R^2$ and $R^3$ are each independently a C6-C18 fatty acid moiety or hydrogen, provided that at least one of $R^1$, $R^2$ or $R^3$ is a C6-C18 fatty acid moiety. In one embodiment, at least one of $R^1$, $R^2$ or $R^3$ is hydrogen. Although structure (I) shows the glyceryl repeating units arranged in a linear fashion, it is understood that the formula also encompasses polyglyceryls which are branched.

Exemplary surfactants useful in the present invention include, but are not limited to, polyglyceryl-10 caprylate/caprate, polyglyceryl-10 caprylate, polyglyceryl-10 caprate, polyglyceryl-10 laurate, as well as analogous substances where the polyglyceryl component contains an average of 8, 9, 11 or 12 glycerol repeating units per molecule. Polyglyceryl esters of C6-C18 fatty acids and polyglyceryl esters of C6-C12 fatty acids suitable for use as surfactants in the present invention are available commercially from various suppliers, such as Lonza.

In various aspects of the invention, the surfactant may have an HLB value of at least 12, 13, or 14 and/or an HLB value of not more than 18, 17 or 16, For example, the HLB value of the surfactant may be 12-18 or 14-16.

In one embodiment of the invention, the only type of surfactant present in the aqueous dispersion is a polyglyceryl ester of C6-C18 or C6-C12 fatty acids or a mixture of such surfactants. In other embodiments, such polyglyceryl esters represent at least 50, 60, 70, 80, 90 or 95% by weight of the total amount of surfactant present.

Surfactant may be combined with water and the organic peroxide in an amount effective to reduce the viscosity of the aqueous dispersion during milling of the organic peroxide. Typically, the concentration of surfactant in the aqueous dispersion is at least 0.1 weight % but no greater than 2.0 weight %.

Other components may be present in the aqueous dispersion in addition to water, surfactant and organic peroxide. For example, to assist in maintaining the product as a stable, homogeneous dispersion and inhibit settling out of the particles of organic peroxide, one or more gelling agents may be incorporated in the aqueous dispersion. A gelling agent is a substance capable of forming a gel when placed in water. Macromolecular gelling agents are particularly useful in the present invention, especially macromolecular gelling agents of natural origin such as certain polysaccharides. Suitable macromolecular gelling agents include, but are not limited to, alginates (salts of alginic acid), carrageenans, gellan gum, guar gum pectic substances (e.g., pectic acid, pectin, pectate), and xanthan gum. Also useful as macromolecular gelling agents are polymers based on acrylic acid, including copolymers of acrylic acid and one or more additional monomers such as (meth)acrylates and functionalized acrylic monomers. Such polymers may be cross-linked. The crosslinking agent may be a comonomer containing two or more carbon-carbon double bonds per molecule capable of participating in free radical polymerization such as a polyalkenylether, divinyl glycol or the like which is copolymerized with one or more monomers such as acrylic acid that contain only one free radically polymerizable carbon-carbon double bond per molecule. Examples of such polymers include the class of polymers referred to as "carbomers" as well as polymers such as those sold under the brand name "Carbopol" by Noveon, Inc.

The gelling agent may be selected such that it is suitable for inclusion in a food or pharmaceutical product. In one embodiment, the gelling agent is capable of being further gelled through crosslinking. For example, a macromolecular gelling agent may contain one or more different types of functional groups along its backbone or pendent to the backbone which are capable of interacting or reacting with a crosslinking agent. Such functional groups may be carboxylic acid groups, sulfonic acid groups or salts thereof (carboxylates, sulfates), for example. Suitable crosslinking agents may include species providing polyvalent cations (e.g., divalent and trivalent cations). Exemplary polyvalent cations include aluminum(3+), barium(2+), calcium(2+), copper(2+), iron(2+), strontium(2+), and zinc(2+). The cations may be supplied in the form of food-safe and; or pharmaceutical-safe salts. Specific examples of suitable salts useful as crosslinking agents include the following, including their hydrates, and mixtures thereof: calcium carbonate, calcium chloride, calcium disodium edetate, calcium lactate, calcium nitrate, calcium oxalate, calcium sulfate, dicalcium phosphate, tricalcium citrate, tricalcium phosphate, and the corresponding barium, copper, strontium, and zinc analogues thereof. The amounts of macromolecular gelling agent and crosslinking agent may be varied as desired.

The gelling agent may be utilized in an amount effective to reduce the tendency of the particulate organic peroxide to settle out of the aqueous dispersion over time. The gelling agent may additionally or alternatively function as a thickener or rheology modifier.

In various embodiments, the aqueous dispersion contains at least 0.25 weight % or at least 0.4 weight % macromolecular gelling agent. In other embodiments, the aqueous dispersion contains not more than 1.5 weight % or not more than 0.75 weight % macromolecular gelling agent. For example, the aqueous dispersion may comprise 0.25 to 1.5 weight % macromolecular gelling agent. The amount of crosslinking agent, if used, may generally be varied in accordance with how much macromolecular gelling agent is present. For example, if the concentration of macromolecular gelling agent is relatively low, the concentration of crosslinking agent may also be relatively low.

In various embodiments, the aqueous dispersion contains at least about 0.1 to 3 weight %, or preferably at least about 0.25 to 1 weight % base or stabilizer or buffer. Examples of suitable bases/stabilizers/buffers include sodium hydroxide, calcium.

hydroxide, magnesium hydroxide, sodium bicarbonate, potassium phosphate (mono and dibasic salts), sodium citrate and the like.

Typical concentrations of crosslinking agent may be, for example, from about 0.01 to 0.075 weight %.

In one embodiment, the composition of the aqueous dispersion is as follows:
  a) 37.5 to 42 weight % benzoyl peroxide having an average particle size of less than 5 μm;
  b) 53.5 to 62 weight % water;
  c) 0.25 to 1.5 weight % macromolecular gelling agent;
  d) 0.1 to 2.0 weight % polyglyceryl ester which contains a polyglycerol moiety having 8 to 12 glycerol repeating units on average which is partially esterified with a mixture of octanoic acid and decanoic acid and has an HLB value of 12-18 (e.g., polyglyceryl-10 caprylate/caprate);
  e) 0.01 to 0.05 weight % salt/crosslinking agent; and
  f) 0 0.25 to 1.0 weight % base/stabilizer/buffer.

The aqueous dispersion may be prepared using any process. For example, the aqueous dispersion may be prepared by milling/grinding an organic peroxide in the presence of water and surfactant until the desired particle size of the organic peroxide is achieved (e.g., less than 20 μm, or less than 15 μm, or less than 10 μm, or less than 5 μm, or between 3 to 5 μm, or 2 to 5 μm, or 1 to 5 μm, or between 3 to 10 μm, or 2 to 10 μm, or 1 to 10 μm). Particle size may be determined using ASTM UOP 856-07, Particle Size Distribution of Powder by Laser Light Scattering and are reported D50 by percent volume.

Milling may be carried out by any suitable equipment known in the art such as a rotor/stator mill, a horizontal ball mill, or, most preferably, a vertical basket mill. The temperature during milling should be controlled so as to avoid decomposition of the organic peroxide. Typically, the milling is conducted at temperatures of 40° C. or less. If a macromolecular gelling agent is to be included in the aqueous dispersion, it may be preferred to add it to the aqueous dispersion after the milling step. The aqueous dispersion also may be prepared using the methods known to those skilled in the art such as those disclosed in U.S. Pat.

No. 4,039,475, 4,092,470, 4,734,135, and 4,440,885, the disclosures of which are incorporated herein in their entireties. Sonication and ultrasound applications/processes known in the art also are suitable.

The aqueous dispersions of the present invention allow for the pumpability and sprayability of the dispersions due to reduced particle size and low viscosity. The aqueous dispersions preferably have a viscosity of between 800-10,000 cps (centipoise), more preferably between 1,000-5,000 cps, and even more preferably between 1,000-2,000 cps determined using a Brookfield viscometer and ASTM D2196-10 (Standard Test Methods for Rheological Properties of Non-Newtonian Materials by Rotational (Brookfield Type) Viscometer. Such dispersions may be sprayed, for example, using pneumatic powered or even hand powered spray devices.

Aqueous dispersions in accordance with the present invention are useful in a wide variety of end use applications where it is desired to utilize organic peroxides, including the food industry as well as the pharmaceutical industry. For example, the aqueous dispersion may be used as a food bleach or as a component of an anti-acne medication. Use of aqueous dispersions in accordance with the present invention alleviate or avoid the problems typically associated with using organic peroxides in dry form, such as difficulties in readily dispersing the peroxide into a composition such as a food product, the generation of dust, and low efficiency in color removal.

In one embodiment, a method of decolorizing a product is provided, comprising contacting the product with an aqueous dispersion in accordance with the present invention. Products suitable for such treatment include food products as well as non-food industrial products. The food product may, for example, be selected from the group consisting of dairy products (e.g., whey, cheese, milk), edible oils, edible fats, polysaccharides (e.g., flour, starch), beverages (e.g., beer) and combinations thereof. Suitable non-food industrial products include, for example, non-edible oils and fats, paper (pulp), textiles and the like. The aqueous dispersion may be contacted with the product in an amount and for a time and at a temperature effective to reduce the color of the product. The conditions selected will depend upon the degree of color reduction desired or necessary as well as the type of product and organic peroxide, among other factors, but the small particle size of the solid organic peroxide present in the aqueous dispersion permits a given amount of color reduction to be achieved within a shorter period of time and/or using a lower amount or concentration of organic peroxide and/or under milder conditions (e.g., a lower contacting temperature) as compared to conventional organic peroxide dispersions or dry peroxide-containing compositions having larger particle sizes.

A pharmaceutical composition may be provided in accordance with the present invention which is comprised of an aqueous dispersion as described herein and at least one additional pharmaceutically acceptable ingredient. Any of the suitable pharmaceutically acceptable ingredients known in the art may be utilized, provided such ingredient is compatible with the organic peroxide. For example, one or more pharmaceutically active ingredients (e.g., antibacterial agents, antimicrobial agents) and/or excipients such as fillers, carriers, surfactants, pigments, stabilizers, rheology control agents, gelling agents and the like may be employed in combination with the aqueous dispersion of organic peroxide. The pharmaceutical composition may be an anti-acne medication and may be in the form of a lotion, soap, gel or cream, for example. Because of the small particle size of the organic peroxide and/or the opportunity to prepare higher concentration dispersions which are still pumpable or pourable, pharmaceutical compositions containing aqueous dispersions in accordance with the present invention may be formulated to be acting or more potent than conventional pharmaceutical compositions containing organic peroxide.

A personal care composition is provided in another embodiment of the invention wherein the personal care composition is comprised of an aqueous dispersion as described herein and at least one additional personal care ingredient. Any of the conventional personal care ingredients known in the art may be combined with the aqueous dispersion of organic peroxide such as, for example, carriers, fillers, surfactants, abrasives, rheology control agents, gelling agents, flavorants, remineralizers, emollients, bleach activators and the like and combinations thereof. The aqueous dispersions of the present invention may, for instance, be used as components of teeth whitening products (e.g., toothpastes, mouth rinses) and hair coloring or bleaching products.

In still another embodiment of the invention, a cleaning product comprised of an aqueous dispersion of organic peroxide as described herein and at least one additional cleaning product ingredient. The cleaning product may, for example, be a dishwasher detergent, a laundry detergent, a laundry bleaching product, a hard surface cleaner (e.g., a cleanser), or the like, in particular products of this type which are in liquid, cream or gel form. Suitable additional cleaning product ingredients include any of the components known to be useful in the aforementioned products, such as surfactants, carriers, bleach activators, builders, abrasives, pigments, rheology control agents, gelling agents, fragrances, anti-deposition agents, enzymes and the like.

The aforementioned products may be prepared by combining an aqueous dispersion of organic peroxide in accordance with the invention with one or more pharmaceutically acceptable ingredients, personal care ingredients or cleaning ingredients.

The organic peroxide-containing aqueous dispersions of the present invention may also be employed as polymerization initiators and hardening agents for thermoset resins and the like.

EXAMPLES

Example 1 (Comparative)

An aqueous dispersion is prepared having the following target composition (amounts listed are weight %):

| | |
|---|---|
| Benzoyl Peroxide | 53.3 |
| Water | 44.15 |
| Gelling agent | 0.5 |
| Decaglycerol Monooleate | 1.5 |
| Crosslinking agent | 0.05 |
| Base | 0.5 |

The surfactant used is Polyaldo 10-1-O decaglycerol monooleate (a polyglyceryl esterified with oleic acid), supplied by Lonza. The benzoyl peroxide used is a benzoyl peroxide/water mixture containing 75 weight % benzoyl peroxide (thus, the actual benzoyl peroxide content of the formulation is 40 weight %). During milling of the benzoyl peroxide to reduce the average particle size to 2 μm, the material forms a very thick paste that significantly slows the milling process. Milling must be interrupted periodically to allow the paste to "rest" and soften sufficiently so that milling can be resumed. This leads to very long milling times in order to mill the benzoyl peroxide to a 2 μm average particle size.

Example 2

In Accordance with the Invention

An aqueous dispersion is prepared having the following target composition amounts listed are weight %):

| Benzoyl Peroxide | 53.3 |
| Water | 45.325 |
| Gelling agent of Ex. 1 | 0.25 |
| Polyglyceryl-10 Caprylate/Caprate | 0.6 |
| Crosslinking agent of Ex. 1 | 0.025 |
| Base of Ex. 1 | 0.5 |

The surfactant used is Polyaldo 10-1-CC, which is described by its supplier Lonza as "decanoic acid, mixed monoesters with decaglycerol and octanoic acid." The benzoyl peroxide used is a benzoyl peroxide/water mixture containing 75 weight % benzoyl peroxide (thus, the actual benzoyl peroxide content of the formulation is 40 weight %). Unexpectedly, improved milling efficiency is afforded by the polyglyceryl-10 caprylate/caprate surfactant as compared to the decaglycerol monooleate surfactant. The most significant improvements are that three times less surfactant is needed and the dispersion remains a free flowing liquid during the entire milling process (i.e., milling does not need to be stopped periodically). Surprisingly, the use of the polyglyceryl-10 caprylate/caprate surfactant allows a 2.5 μm average particle size to be reached twice as fast compared to when the decaglycerol monooleate is used as the surfactant, even at the reduced level of surfactant of Example 2. Since the product remains fluid throughout the entire process, temperature control is much better and the danger of decomposition significantly reduced. Due to the lower level of surfactant, less gelling agent (carrageenan) is needed in order to stabilize the dispersion. Since less carrageenan is needed, it is much easier to disperse homogeneously into the paste obtained by milling.

The following examples illustrate certain of the advantages provided by the aqueous dispersions of the present invention.

Example 3

Dispersion of Organic Peroxide into a Food Product

In a conventional process for treating a whey stream with a dry organic peroxide (such as an organic peroxide in admixture with an inert support), a 25 kg box of the dry organic peroxide is lifted and dumped into a high shear mixer in order to be dispersed in water. Care must be taken to avoid settling of the organic peroxide. The tank must be continuously stirred. The resulting mixture is then metered into a whey stream.

An aqueous dispersion of the present invention, which is in pre-dispersed liquid form, may be utilized as follows. A dip tube is inserted into a 55 gallon drum that contains the inventive aqueous dispersion. The aqueous dispersion containing the organic peroxide is then directly metered into the whey stream. There is no need to left heavy boxes by hand (thereby avoiding possible ergonomic issues) and it is easy to achieve the addition of a uniform concentration of the organic peroxide to the food product stream. The stirred tank is eliminated, thereby simplifying the process and lowering capital costs. There is no need to add water and disperse; the possibility of operator error is thus eliminated.

Example 4

Elimination of Dusting

This example illustrates how the aqueous dispersion of the present invention solves the dusting issue encountered with dry organic peroxide products.

In a traditional process, a 25 kg box of a dry organic peroxide in particulate form (e.g., in admixture with an inert support) is opened and lifted to dump into a stirred tank. In the process, some powder (containing organic peroxide) becomes airborne and creates a dust cloud. The dust settles on surfaces surrounding the operation. The operator should be outfitted with a dust mask and ventilation (e.g., a dust collector) is positioned over the tank in order to reduce the amount of dust which escapes from the operation, as the dust is an inhalation hazard and skin irritant and can potentially cause a dust explosion. To clean up the settled dust, it may be wetted down with water to render it sae for clean-up. The wetted dust, containing organic peroxide, is then absorbed using cloths and mops, for example. The waste material is collected to a drum for disposal.

When using an aqueous dispersion of organic peroxide in accordance with the present invention, a dip tube may be simply inserted into a drum of the aqueous dispersion and the aqueous dispersion metered directly into a process stream, such as a stream containing a food product (e.g., whey). There is no manual handling of the organic peroxide and no dust is created. As the organic peroxide remains stably dispersed, no stirring or agitation of the drum contents is needed. If some amount of aqueous dispersion is spilled as a result of tube transfer between drums, such amount is likely to be small and readily contained. The spilled amount may be cleaned up with a damp cloth and bagged for disposal.

Example 5

Treatment of Spill

In the course of handling, a 25 kg box of conventional dry organic peroxide spills. The resulting dust cloud contaminates the entire surrounding area, including all equipment, fixtures, ceiling and floor. Approximately 30 gallons of water is needed to wet down all of these surfaces. The wet powder containing the spilled organic peroxide is shoveled into three 55 gallon drums, wherein the clean-up operation takes about five hours. The contaminated area is cleaned with soap and water.

In the event a 55 gallon drum of an aqueous dispersion in accordance with the present invention is accidentally spilled, there is no need to pre-wet the organic peroxide. The spilled material may be directly absorbed using an aborptive material, such as SnakeBOOM (available from Breg Environmental). The used absorptive material is placed into three 55 gallon drums for disposal. The clean-up takes about two hours. The area of the spill is cleaned with soap and water.

Example 6

Improvement in Decolorization Efficiency

This example demonstrates the improvements in efficiency which are possible when using an aqueous dispersion in accordance with the present invention in a decolorization process.

In a conventional whey stream decolorization process, a quantity of benzoyl peroxide in admixture with a solid inert support which has been dispersed in water is metered into a whey stream and the resulting mixture enters into a heated stirred tank where it is held at 60° C. for 45 minutes in order to achieve a desired level of color reduction in the whey stream.

Using an aqueous dispersion in accordance with the present invention containing benzoyl peroxide of smaller particle size than is present in the aforementioned conventional benzoyl peroxide/inert support admixture dispersion, the aqueous dispersion is metered into the whey stream and the resulting mixture enters a heat exchanger. Achieving the same level of color reduction as in the aforementioned comparative example is expected to take significantly less time at 60° C. than in the comparative example.

What is claimed is:

1. A composition comprising:
 a) an aqueous pumpable, pourable, or sprayable dispersion having a viscosity between 800 and 2000 centipoise, based on said dispersion, and which is shear thinning and sufficiently fluid such that it is capable of being poured without subjection to stirring, comprised of:
  i) about 35% by weight or more, based on said dispersion, of water insoluble, solid benzoyl peroxide having an average particle size of less than 10 μm,
  ii) 0.1 weight % to 2 weight % surfactant, based on said dispersion, which is a polyglyceryl ester of one or more C6-C12 fatty acids selected from the group consisting of octanoic acid, decanoic acid, and mixtures thereof, wherein the surfactant has an HLB value of 12 to 18;
 b) optionally, at least one additional pharmaceutically acceptable component, and
 c) optionally, one or more excipients.

2. The composition of claim 1, wherein the at least one pharmaceutically acceptable component is selected from the group consisting of antibacterial agents, antimicrobial agents, and bleach activators.

3. The composition of claim 1 comprising at least one pharmaceutically acceptable component selected from the group consisting of pharmaceutically active ingredients.

4. The composition of claim 1 comprising at least one excipient selected from the group consisting of fillers, carriers, surfactants, pigments, stabilizers, rheology control agents, gelling agents, flavorants, remineralizers, and emollients.

5. The composition of claim 1 comprising at least one additional pharmaceutically acceptable component that is a pharmaceutically active ingredient, at least one excipient, and optionally water.

6. The composition of claim 1, wherein the polyglyceryl ester of one or more C6-C12 fatty acids contains a polyglyceryl moiety having 8 to 12 glycerol repeating units on average.

7. The composition of claim 1, wherein the surfactant is based on a polyglyceryl having hydroxyl groups with from about 25% to about 60% of the hydroxyl groups of the polyglyceryl being esterified.

8. The composition of claim 1, wherein the surfactant is a polyglyceryl-10 caprylate/caprate.

9. The composition of claim 1, wherein the surfactant is a pharmaceutically acceptable surfactant.

10. The composition of claim 1, wherein the solid benzoyl peroxide has an average particle size of less than 5 μm.

11. The composition of claim 1, wherein the surfactant has structure (I):
 $R^1$—[$CH_2$—$CH(OR^2)$—$CH_2O$]$_n$—$R^3$ wherein the average value of n is from about 6 to about 14 and $R^1$, $R^2$ and $R^3$ are each independently a C8 or C10 fatty acid moiety or hydrogen, provided that at least one of $R^1$, $R^2$ or $R^3$ is a C8 or C10 fatty acid moiety.

12. The composition of claim 1, wherein the composition is an anti-acne composition.

13. The composition of claim 1, wherein the composition is a teeth whitening composition.

14. The composition of claim 1, wherein the composition is a hair coloring or hair bleaching composition.

15. The composition of claim 1, wherein the composition is a paste, lotion, soap, gel or cream.

16. The composition of claim 1, wherein the aqueous dispersion remains fluid during milling and stably dispersed thereafter, and which has a viscosity between 800 and 2000 centipoise and is shear thinning, comprises:
 about 37 to about 42 weight %, based on said dispersion, benzoyl peroxide having an average particle size of less than 5 μm;
 about 53 to about 62 weight %, based on said dispersion, water;
 about 0.2 to about 2 weight %, based on said dispersion, gelling agent;
 about 0.1 to about 2 weight % polyglyceryl ester, based on said dispersion, which contains a polyglycerol moiety having 8 to 12 glycerol repeating units on average which is partially esterified with a mixture of octanoic acid and decanoic acid and has an HLB value of 12-18;
 about 0.01 to about 0.05 weight %, based on said dispersion, crosslinking agent; and
 about 0.2 to about 1 weight %, based on said dispersion, base.

17. A composition derived from a process comprising the step of combining:
 a) an aqueous pumpable, pourable, or sprayable dispersion having a viscosity between 800 and 2000 centipoise and which is shear thinning and sufficiently fluid such that it is capable of being poured without subjection to stirring, comprised of:
  i) about 35% by weight or more, based on said dispersion, of water insoluble, solid benzoyl peroxide having an average particle size of less than 10 μm,
  ii) 0.1 weight % to 2 weight % surfactant, based on said dispersion, which is a polyglyceryl ester of one or more C6-C12 fatty acids selected from the group consisting of octanoic acid, decanoic acid, and mixtures thereof, wherein the surfactant has an HLB value of 12 to 18;
 with either
 b) at least one additional pharmaceutically acceptable component,
 or
 c) one or more excipients.

* * * * *